United States Patent [19]

Chambers

[11] Patent Number: 5,410,049
[45] Date of Patent: Apr. 25, 1995

[54] BENZODIAZEPINE DERIVATIVES, COMPOSITIONS CONTAINING THEM AND THEIR USE IN THERAPY

[75] Inventor: Mark S. Chambers, Watford, England

[73] Assignee: Merck Sharpe & Dohme Ltd., Hoddesdon, England

[21] Appl. No.: 992,217

[22] Filed: Dec. 17, 1992

[30] Foreign Application Priority Data

Dec. 20, 1991 [GB] United Kingdom ............. 9127115
Aug. 13, 1992 [GB] United Kingdom ............. 9217158

[51] Int. Cl.$^6$ ............. C07D 243/24; A61K 31/55
[52] U.S. Cl. ............. 540/504; 514/221
[58] Field of Search ............. 540/473, 504; 514/221

[56] References Cited

U.S. PATENT DOCUMENTS 4,820,834  4/1989  Evans et al. ............. 540/504
5,004,741  4/1991  Evans et al. ............. 514/221

FOREIGN PATENT DOCUMENTS

0167919A2  1/1986  European Pat. Off.

*Primary Examiner*—Nicholas Rizzo
*Attorney, Agent, or Firm*—Robert J. North; Joseph F. DiPrima

[57] ABSTRACT

Compounds of formula (I), and salts and prodrugs thereof

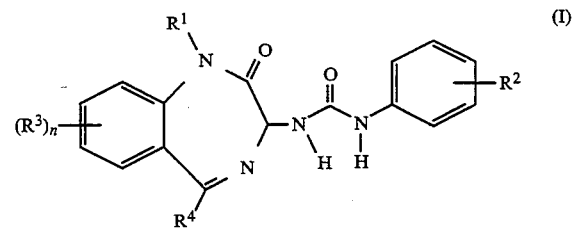

wherein:
  $R^1$ is H, certain optionally substituted $C_{1-6}$alkyl, or $C_{3-7}$cyclocalkyl;
  $R^2$ represents a group

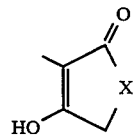

wherein X is O, S or $NR^8$ where $R^8$ is H or $C_{1-4}$alkyl;
  $R^3$ is $C_{1-6}$alkyl, halo or $NR^6R^7$;
  $R^4$ is $C_{1-7}$alkyl, $C_{3-7}$cycloalkyl, $C_{4-7}$cycloalkylalkyl or optionally substituted aryl;
  n is 0, 1, 2 or 3; are CCK and/or gastrin receptor antagonists. They and compositions thereof are useful in therapy.

6 Claims, No Drawings

BENZODIAZEPINE DERIVATIVES, COMPOSITIONS CONTAINING THEM AND THEIR USE IN THERAPY

This invention relates to benzodiazepine compounds which are useful as antagonists of cholecystokinin and gastrin receptors.

Cholecystokinins (CCK) and gastrin are structurally related peptides which exist in gastrointestinal tissue and in the central nervous system (see, V. Mutt, *Gastrointestinal Hormones,* G.B.J. Green, Ed., Raven Press, N.Y., p.169 and G. Nission, ibid. p.127).

Cholecystokinins include CCK-33, a neuropeptide of thirty-three amino acids in its originally isolated form (see, Mutt and Jorpes, *Biochem. J.* 125, 678 (1971)), its carboxylterminal octapeptide, CCK-8 (also a naturally-occurring neuropeptide and the minimum fully active sequence), and 39- and 12-amino acid forms. Gastrin occurs in 34-, 17- and 14-amino acid forms, with the minimum active sequence being the C-terminal tetrapeptide, Trp-Met-AsP-Phe-$NH_2$, which is the common structural element shared by both CCK and gastrin.

CCKs are believed to be physiological satiety hormones, thereby possibly playing an important role in appetite regulation (G. P. Smith, *Eating and Its Disorders,* A. J. Stunkard and E. Stellar, Eds, Raven Press, New York, 1984, p. 67), as well as stimulating colonic motility, gall bladder contraction, pancreatic enzyme secretion and inhibiting gastric emptying. They reportedly co-exist with dopamine in certain mid-brain neurons and thus may also play a role in the functioning of dopaminergic systems in the brain, in addition to serving as neurotransmitters in their own right (see A. J. Prange et al., "Peptides in the Central Nervous System", *Ann. Repts. Med. Chem* 17, 31, 33[1982] and references cited therein; J. A. Williams, *Biomed Res.* 3 107 [1982]; and J. E. Morley, *Life Sci.* 30, 479[1982]).

The primary role of gastrin, on the other hand, appears to be stimulation of the secretion of water and electrolytes from the stomach and, as such, is involved in control of gastric acid and pepsin secretion. Other physiological effects of gastrin then include increased mucosal blood flow and increased antral motility. Rat studies have shown that gastrin has a positive trophic effect on the gastric mucosa, as evidenced by increased DNA, RNA and protein synthesis.

There are at least two subtypes of cholecystokinin receptors termed CCK-A and CCK-B (T. H. Moran et al., "Two brain cholecystokinin receptors: implications for behavioural actions", *Brain Res.,* 362, 175–79[1986]). Both subtypes are found both in the periphery and in the central nervous system.

CCK and gastrin receptor antagonists have been disclosed for preventing and treating CCK-related and/or gastrin related disorders of the gastrointestinal (GI) and central nervous (CNS) systems of animals, especially mammals, and more especially those of humans. Just as there is some overlap in the biological activities of CCK and gastrin, antagonists also tend to have affinity for both CCK-B receptors and gastrin receptors. Other antagonists have activity at the CCK-A subtype.

Selective CCK antagonists are themselves useful in treating CCK-related disorders of appetite regulatory systems of animals as well as in potentiating and prolonging opiate-mediated analgesia [see P. L. Faris et al., *Science* 226, 1215 (1984)], thus having utility in the treatment of pain. CCK-B and CCK-A antagonists have also been shown to have a direct analgesic effect [M. F. O'Neill et al., *Brain Research,* 534 287 (1990)]. Selective CCK and gastrin antagonists are useful in the modulation of behaviour mediated by dopaminergic and serotonergic neuronal systems and thus have utility in the treatment of schizophrenia and depression (Rasmussen et. al., 1991, *Eur. J. Pharmacol.,* 209, 135–138; Woodruff et. al., 1991, *Neuropeptides,* 19, 45–46; Cervo et. al., 1988, *Eur. J. Pharmacol.,* 158, 53–59), as a palliative for gastrointestinal neoplasms, and in the treatment and prevention of gastrin-related disorders of the gastrointestinal system in humans and animals, such as peptic ulcers, Zollinger-Ellison syndrome, antral G cell hyperplasia and other conditions in which reduced gastrin activity is of therapeutic value, see e.g. U.S. Pat. No. 4,820,834. Certain CCK antagonists are useful anxiolytic agents and can be used in the treatment of panic and anxiety disorders.

CCK has been reported to evoke the release of stress hormones such as adrenocorticotrophic hormone, $\beta$-endorphin, vasopressin and oxytocin, CCK may function as a mediator of responses to stress and as part of the arousal system. CCK-A receptors are now known to be present in a number of areas of the CNS and may be involved in modulating all of the above.

CCK may be involved in the regulation of stress and its relationship with drug abuse e.g. alleviation of the benzodiazepine withdrawal syndrome (Singh et. al., 1992, *Br. J. Pharmacol.,* 105, 8–10) and neuroadaptive processes.

Since CCK and gastrin also have trophic effects on certain tumours [K. Okyama, *Hokkaido J. Med. Sci.,* 206–216 (1985)], antagonists of CCK and gastrin are useful in treating these tumours [see, R. D. Beauchamp et al., Ann. Surg., 202, 203 (1985)].

In the light of discussion in C. Xu et al., *Peptides.,* 8, 1987, 769–772, CCK antagonists may also be effective in neuroprotection.

CCK receptor antagonists have been found to inhibit the contractile effects of CCK on iris sphincter and ciliary muscles of monkey and human eyes (Eur. J. Pharmacol., 211(2), 183–187; A. Bill et al., Acta Physiol. Scand., 138, 479–485[1990]), thus having utility in inducing miosis for therapeutic purposes.

European patent application no. 0 167 919 discloses benzodiazepine CCK and gastrin antagonists substituted in the 3-position by, inter alia, a phenyl urea and at the 5-position by an optionally substituted phenyl or pyridyl group. There is no suggestion of the phenyl urea substitution of the compounds of the present invention.

The present invention provides benzodiazepine compounds of formula (I)

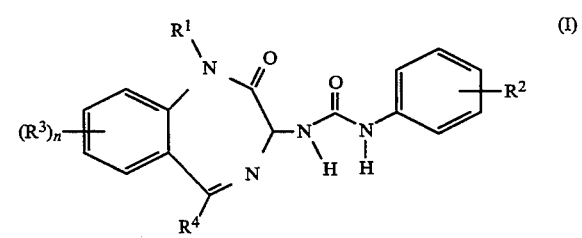

wherein:

$R^1$ represents H, $C_{1-6}$alkyl, $C_{3-4}$cycloalkyl, cyclopropylmethyl, $CH_2CO_2R^5$ (where $R^5$ is $C_{1-4}$alkyl) or a group $CH_2CONR^6R^7$ (where $R^6$ and $R^7$ each independently represents H or $C_{1-4}$alkyl, or $R^6$ and $R^7$ together form a chain $(CH_2)p$ where p is 4 or 5);

$R^2$ represents a group

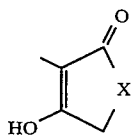

wherein:

X represents O, S or $NR^8$ where $R^8$ represents H or $C_{1-4}$alkyl;

each $R^3$ represents $C_{1-6}$alkyl, halo or $NR^6R^7$, where $R^6$ and $R^7$ are as previously defined;

$R^4$ represents $C_{1-6}$alkyl, $C_{3-7}$cycloalkyl, $C_{4-7}$cycloalkylalkyl or aryl optionally substituted by one or more substituents selected from $C_{1-4}$alkyl, $C_{1-4}$alkoxy, hydroxy, halo and trifluoromethyl;

n is 0, 1, 2 or 3;

and salts and prodrugs thereof.

It will be appreciated that formula (I) is intended to embrace all possible isomers, including optical isomers, and mixtures thereof, including racemates.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bungaard, Elsevier, 1985.

As used herein, alkyl means linear or branched chain alkyl. Examples of suitable alkyl groups include methyl, ethyl, isopropyl and isobutyl groups.

When $R^1$ represents cycloalkyl, examples of suitable cycloalkyl groups include cyclopropyl, cyclopentyl and cyclohexyl groups, preferably cyclopropyl.

Halo includes fluoro, chloro and bromo. Preferably halo will be fluoro or chloro.

Where $R^4$ is aryl this may be a 5- or 6-membered aromatic ring system, optionally containing one or more heteroatoms such as O, S or N, for example, pyridyl, thienyl or phenyl.

One subgroup of compounds according to the invention is represented by compounds of formula II) wherein $R^1$ represents $C_{1-6}$alkyl, $C_{3-7}$cycloalkyl, cyclopropylmethyl, $CH_2CO_2R^5$ or a group $CH_2CONR^6R^7$; $R^3$ represents $C_{1-6}$alkyl or halo; and n is 0 or 1.

Preferably $R^1$ is $C_{1-6}$alkyl, such as $C_{1-4}$alkyl, for example, methyl, n-propyl or isobutyl. More preferably $R^1$ is methyl.

Preferably X is S or $NR^8$, more preferably $NR^8$ such as NH or $NCH_3$.

Preferably $R^2$ is in the 3- or 4-position of the phenyl ring, more preferably the 3-position.

Suitable values for $R^3$ include methyl and dimethylamino.

Preferably n is 0.

Suitable values for $R^4$ include methyl, ethyl, i-propyl, t-butyl, cyclobutyl, cyclopentyl, cyclohexyl, cycloheptyl, 4-pyridyl and phenyl. Preferably $R^4$ represents $C_{4-7}$ cycloalkyl, such as cyclobutyl, cyclopentyl or cyclohexyl, or unsubstituted phenyl. More preferably $R^4$ represents cyclohexyl.

A preferred sub class of compounds of formula (I) is represented by compounds of formula (IA):

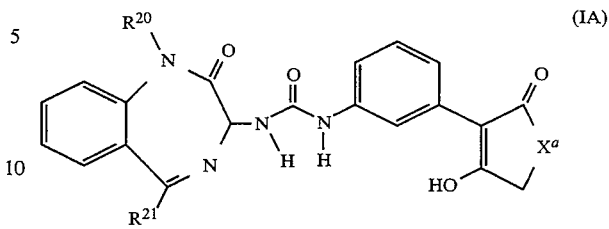

wherein $X^a$ is S or $NR^8$, where $R^8$ is as previously defined;

$R^{20}$ is $C_{1-6}$alkyl, preferably $C_{1-4}$alkyl;

$R^{21}$ is $C_{3-7}$cycloalkyl, preferably $C_{4-7}$cycloalkyl; and salts and prodrugs thereof.

Preferably the salts of the compounds of formula (I) are pharmaceutically acceptable, but non-pharmaceutically acceptable salts may be used for the preparation of pharmaceutically acceptable salts. The pharmaceutically acceptable salts of the compounds of formula (I) include the conventional non-toxic salts or the quaternary ammonium salts of the compounds from formula (I) formed, e.g., from non-toxic inorganic or organic salts. For example, such conventional non-toxic salts include basic salts, e.g. sodium and potassium salts.

The pharmaceutically acceptable salts of the present invention can be synthesized from the compounds of formula (I) which contain an acidic moiety by conventional chemical methods. Generally, the salts are prepared by reacting the free acid with stoichiometric amounts or with an excess of the desired salt-forming inorganic or organic base in a suitable solvent or various combinations of solvents.

The present invention also encompasses a pharmaceutical composition comprising a compound of formula (I), or a salt or prodrug thereof and a pharmaceutically acceptable carrier or diluent.

The compounds of formula (I) and their salts and prodrugs, may be administered to animals, preferably to mammals, and most especially to a human subject either alone or, preferably, in combination with pharmaceutically acceptable carriers or diluents, optionally with known adjuvants, such as alum, in a pharmaceutical composition, according to standard pharmaceutical practice. The compounds can be administered orally, parentally, including by intravenous, intramuscular, intraperitoneal or subcutaneous administration, or topically.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavouring agents may be added.

For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

For topical administration, a compound of formula (I) may be formulated as, for example, a suspension, lotion, cream or ointment.

For topical administration, pharmaceutically acceptable carriers are, for example, water, mixtures of water and water-miscible solvents such as lower alkanols or arylalkanols, vegetable oils, polyalkylene glycols, petroleum based jelly, ethyl cellulose, ethyl oleate, carboxymethylcellulose, polyvinylpyrrolidone, isopropyl myristate and other conventionally-employed non-toxic, pharmaceutically acceptable organic and inorganic carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like.

The compounds of formula (I) antagonise CCK and/or gastrin and are useful for the treatment and prevention of disorders including central nervous system disorders wherein CCK and/or gastrin may be involved. Examples of such disease states include gastrointestinal diseases, including gastrointestinal ulcers, such as peptic and duodenal ulcers, irritable bowel syndrome, gastroesophagenal reflux disease or excess pancreatic or gastrin secretion, acute pancreatitis, or motility disorders; central nervous system disorders, including central nervous system disorders caused by CCK interaction with dopamine, serotonin and other monoamine neurotransmitters, such as neuroleptic disorders, tardive dyskinesia, Parkinson's disease, psychosis or Gilles de la Tourette syndrome; depression, such as depression resulting from organic disease, secondary to stress associated with personal loss or idiopathic depression; schizophrenia; disorders of appetite regulatory systems; Zollinger-Ellison syndrome, antral and cell hyperplasia, or pain.

The compounds of formula (I) are particularly useful in the treatment or prevention of neurological disorders involving anxiety disorders and panic disorders, wherein CCK and/or gastrin is involved. Examples of such disorders include panic disorders, anxiety disorders, panic syndrome, anticipatory anxiety, phobic anxiety, panic anxiety, chronic anxiety and endogenous anxiety.

The compounds of formula (I) are also useful for directly inducing analgesia, opiate or non-opiate mediated, as well as anaesthesia or loss of the sensation of pain.

The compounds of formula (I) may further be useful for preventing or treating the withdrawal response produced by chronic treatment or abuse of drugs or alcohol. Such drugs include, but are not limited to benzodiazepines, cocaine, alcohol and nicotine.

The compounds of formula (I) may further by useful in the treatment of stress and its relationship with drug abuse.

The compounds of formula (I) may further be useful in the treatment of oncologic disorders wherein CCK may be involved. Examples of such oncologic disorders include small cell adenocarcinomas and primary tumours of the central nervous system glial and neuronal cells. Examples of such adenocarcinomas and tumours include, but are not limited to, tumours of the lower oesophagus, stomach, intestine, colon and lung, including small cell lung carcinoma.

The compounds of formula (I) may also be useful as neuroprotective agents, for example, in the treatment and/or prevention of neurodegenerative disorders arising as a consequence of such pathological conditions as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Amyotrophic Lateral Sclerosis, Parkinson's disease, Olivo-ponto-cerebellar atrophy, anoxia such as from drowning, spinal cord and head injury, and poisoning by neurotoxins, including environmental neurotoxins.

The compounds of formula (I) may further be used to induce miosis for therapeutic purposes after certain types of examination and intraocular surgery. An example of intraocular surgery would include cateract surgery with implantation of an artificial lens. The CCK antagonist compounds of this invention can be used to prevent miosis occuring in association with iritis, ureitis and trauma.

The present invention therefore provides a compound of formula (I) or a salt or prodrug thereof for use in the preparation of a medicament.

The present invention also provides a compound of formula (I), or a salt or prodrug thereof, for use in therapy.

In a further or alternative embodiment the present invention provides a method for the treatment or prevention of a physiological disorder involving CCK and/or gastrin which method comprises administration to a patient in need thereof of a CCK and/or gastrin antagonising amount of a compound of formula (I).

When a compound according to formula (I) is used as an antagonist of CCK or gastrin in a human subject, the daily dosage will normally be determined by the prescribing physician with the dosage generally varying according to the age, weight, and response of the individual patient, as well as the severity of the patient's symptoms. However, in most instances, an effective daily dosage will be in the range from about 0.005 mg/kg to about 100 mg/kg of body weight, and preferably, of from 0.05 mg/kg to about 50 mg/kg, such as from about 0.5 mg/kg to about 20 mg/kg of body weight, administered in single or divided doses. In some cases, however, it may be necessary to use dosages outside these limits. For example, animal experiments have indicated that doses as low as 1 ng may be effective.

In effective treatment of panic syndrome, panic disorder, anxiety disorder and the like, preferably about 0.05 mg/kg to about 0.5 mg/kg of CCK antagonist may be administered orally (p.o.), administered in single or divided doses per day (b.i.d.). Other routes of administration are also suitable.

For directly inducing analgesia, anaesthesia or loss of pain sensation, the effective dosage preferably ranges from about 100 ng/kg to about 1 mg/kg by intravenous administration. Oral administration is an alternative route, as well as others.

In the treatment or irritable bowel syndrome, preferably about 0.1 to 10 mg/kg of CCK antagonist is administered orally (p.o.), administered in single or divided doses per day (b.i.d.). Other routes of administration are also suitable.

The use of a gastrin antagonist as a tumour palliative for gastrointestinal neoplasma with gastrin receptors, as a modulator of central nervous activity, treatment of Zollinger-Ellison syndrome, or in the treatment of peptic ulcer disease, an effective dosage of preferably about 0.1 to about 10 mg/kg administered one-to-a-four times daily is indicated.

For use as neuroprotective agents the effective dosage preferably ranges from about 0.5 mg/kg to about 20 mg/kg.

Because these compounds antagonise the function of CCK in animals, they may also be used as feed additives to increase the food intake of animals in daily dosage of preferably about 0.05 mg/kg to about 50 mg/kg of body weight.

The compounds of formula (I) may be prepared by processes analogous to those described in European Patent Specification No. 0284256. For example, according to one general process (A), a compound of formula (I) may be prepared by reaction of an intermediate of formula (II) with a compound of formula (III)

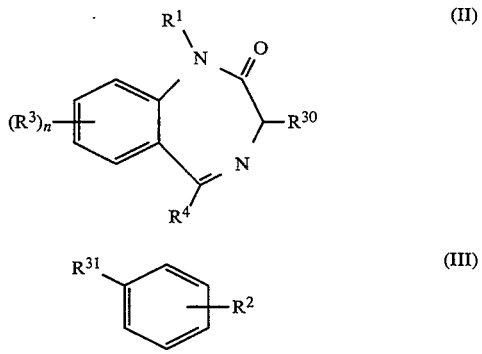

wherein $R^1$, $R^2$, $R^3$, $R^4$ and n are as defined for formula (I), one of $R^{30}$ and $R^{31}$ represents $NH_2$ and the other of $R^{30}$ and $R^{31}$ represents $N=C=O$.

The reaction is preferably conducted in a suitable organic solvent, such as an ether, for example, tetrahydrofuran, at room temperature.

According to a further general process, (B), compounds of formula (I) may be prepared by reacting a compound of formula (IV):

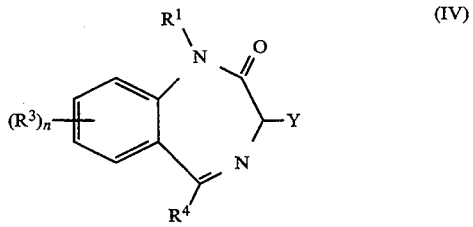

wherein $R^1$, $R^3$, $R^4$ and n are as defined for formula (I) and Y represents an activated carbamate, with an amine of formula (III) wherein $R^{31}$ is $NH_2$ (IIIA), in the presence of a base. Suitably Y may represent an appropriately substituted aryl carbamate of formula

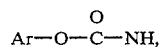

for example

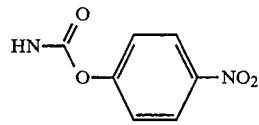

Suitable bases for use in the reaction include tertiary amines, for example, triethylamine.

The reaction is conveniently effected in a suitable organic solvent, for example, dimethylformamide, at ambient or elevated temperature. Preferably the reaction is conducted at approximately 50° C.

Intermediates of formula (IV) may be prepared from amines of formula (II) wherein $R^{30}$ is $NH_2$ (IIA) by reaction with a suitable haloformate of formula

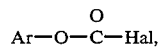

where Hal is halo, such as chloro or bromo for example

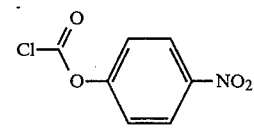

in the presence of a base, such as a tertiary amine, for example, triethylamine.

Intermediates of formula (II) wherein $R^{30}$ is $N=C=O$ (IIB) may be prepared from the corresponding amines of formula (II) wherein $R^{30}$ is $NH_2$ by conventional methods, for example, by treatment with triphosgene.

Intermediates of formula (IIA) may be prepared from compounds of formula (VI)

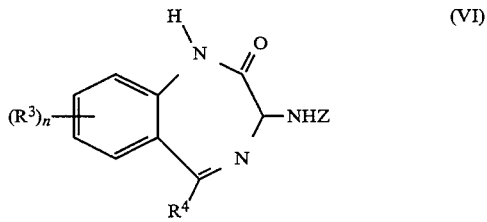

wherein $R^3$, $R^4$ and n are as defined for formula (I) and Z is a protecting group; by reaction with a reagent suitable to introduce the group $R^1$, for example a halide of formula $R^1Hal$ where Hal represents halo such as bromo or iodo, in the presence of a base, such as an alkali metal hydride or an alkaline earth metal carbonate, for example sodium hydride or caesium carbonate; or a suitable dialkyl acetal of dimethyl formamide in a suitable organic solvent, e.g. toluene followed by deprotection.

Compounds of formula (VI) may be prepared from compounds of formula (VII)

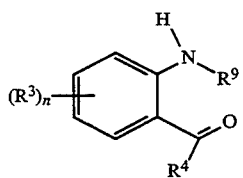

wherein $R^3$, $R^4$ and n are as defined for formula (I) and $R^9$ is H, by a reaction sequence comprising:

(i) reaction with a compound of formula (VIII)

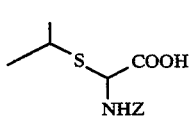

wherein Z is as defined above, in the presence of a base, such as a tertiary amine, for example triethylamine or N-methyl morpholine, and a coupling reagent. Any of the coupling reagents commonly used in peptide synthesis are suitable, for example, 1,3-dicyclohexylcarbodiimide (DCC) or isobutyl chloroformate;

(ii) Treatment with gaseous ammonia, preferably in the presence of a mercury containing catalyst, such as mercury(II) chloride. The reaction is conveniently effected in a suitable organic solvent, such as an ether, for example, tetrahydrofuran;

(iii) Treatment with an organic acid, for example acetic or propionic acid, optionally in the presence of an ammonium salt, for example ammonium acetate.

Compounds of formula (VII) wherein $R^9$ is H may be prepared from corresponding compounds of formula (VII) wherein $R^9$ is $COCH_3$ by treatment with a mineral acid, for example hydrochloric acid, or base hydrolysis, for example, using aqueous sodium hydroxide. The reaction is conveniently affected in refluxing methanol.

Compounds of formula (VII) wherein $R^9$ is $COCH_3$ may be prepared from compounds of formula (IX)

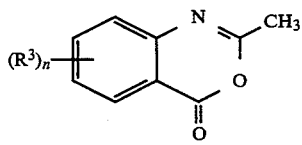

wherein $R^3$ and n are defined as for formula (I), by reaction with a Grignard reagent of formula $R^4MgHal$ wherein Hal is halo such as chloro, bromo or iodo.

Compounds of formula (IX) may be prepared by known methods, e.g. see D. A. Walsh, Synthesis, 677, (1980).

Alternatively, compounds of formula (VII) wherein $R^9$ is H may be prepared by reaction of a compound of formula (X)

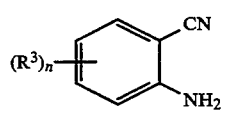

wherein $R^3$ and n are as previously defined, with a Grignard reagent of formula $R^4MgHal$ wherein $R^4$ is as previously defined and Hal is halo such as chloro, bromo or iodo.

Compounds of formula (X) are commercially available or may be prepared from commercially available compounds by conventional methods.

Intermediates of formula (III) wherein $R^{31}$ represents $N=C=O$ (IIIB) may be prepared from the corresponding amines of formula (III) wherein $R^{31}$ is $NH_2$ (IIA) by conventional methods, such as reaction with triphsogene.

Amines of formula (IIIA) may be prepared from the corresponding nitro compounds of formula (XI)

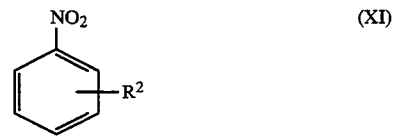

wherein $R^2$ is as defined for formula (I), by reduction.

Suitably the reduction is effected by catalytic hydrogenation, for example, using a noble metal catalyst such as palladium which may be supported, e.g. on carbon. The reaction is conveniently effected in a suitable organic solvent, such as an alcohol, e.g. ethanol.

Compounds of formula (XI) may be prepared from intermediates of formula (XII)

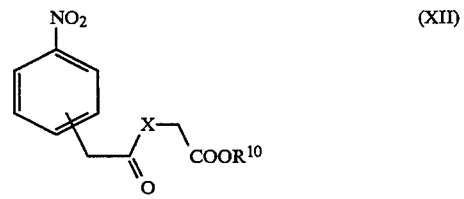

wherein X is as defined for formula (I) and $R^{10}$ represents $C_{1-6}alkyl$, by treatment with a base.

Suitable reaction conditions are chosen depending on the nature of X. For example, when X is $NR^8$, suitable bases include alkaline metal alkoxides, such as sodium methoxide. This reaction is conveniently effected in a suitable organic solvent, such as an alcohol, e.g. methanol, conveniently at elevated temperature, for example, the reflux temperature of the solvent. When X is O or S a particularly favoured base is 1,8-diazabicyclo[5.4.-0]undec-7-ene (DBU). This reaction is preferably conducted at room temperature.

Intermediates of formula (XII) wherein X is $NR^8$ may be prepared from compounds of formula (XIIIA)

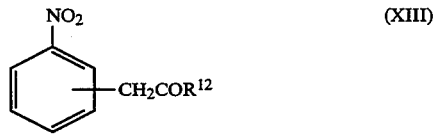

wherein $R^{12}$ is hydroxy (XIIIA) by reaction with a compound of formula $R^{10}O_2CCH_2NR^8H$, or a salt thereof, in the presence of a coupling reagent.

Suitable coupling reagents include those used in peptide synthesis, and in particular 1-(3-dimethylaminopropyl)-3-ethylcarbodiimide hydrochloride (EDC).

Advantageously an acylation catalyst, such as 4-dimethylaminopyridine (DMAP), is added to the reaction mixture.

Intermediates of formula (XII) wherein X is O or S may be prepared from compounds of formula (XIIIB)

wherein $R^{12}$ is halo, e.g. chloro, (XIIIB) by reaction with a compound of formula $R^{10}O_2CH_2XH$ in the presence of a base.

Suitable bases of use in the reaction include tertiary amines, such as triethylamine.

Compounds of formula (XIIIA) are commercially available.

Compounds of formula (XIIIB) may be prepared from compounds of formula (XIIIA) by conventional procedures well known to those skilled in the art such as, for example, treatment with oxalyl chloride.

Where the above-described process for the preparation of the compounds according to the invention gives rise to mixtures of stereoisomers these isomers may, if desired, be separated, suitably by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (−)-di-p-toluoyl-L-tartaric acid and/or (+)-di-p-toluoyl-D-tartaric acid followed by fractional crystallization and regeneration of the free base. The novel compounds may also be resolved by formation of diastereomeric esters or amides, followed by chromatographic separation and removal of the chiral auxiliary. Alternatively, enantiomers of the novel compounds may be separated by HPLC using a chiral column.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wutts, *Protective Groups in Organic Synthesis*, John Wiley & Sons, 1991. The protecting groups may be removed at a convenient subsequent stage using methods known from the art.

The following examples are provided to assist in a further understanding of the invention. Particular materials employed, species and conditions are intended to be further illustrative of the invention and not limitative of the scope thereof.

EXAMPLE 1

N-[3(R,S)-5-Cyclohexyl-2,3,dihydro-1-methyl-2-oxo-1H-1,4-benzodiazepin-3-yl]N', [3-(2,5,dihydro-4-hydroxy-2-oxothien,3-yl)phenyl]urea Step 1: S-(3-Nitrophenylacetyl)thiolacetic acid methyl ester To a stirred solution of 3-nitrophenylacetic acid (10 g, 0.055 mol) in dichloromethane (200 ml) at 0° C., was added oxalyl chloride (5.3 ml, 0.55 mol) dropwise. After addition was complete the mixture was allowed to warm to room temperature and stirred for 2 h. The solvent was evaporated in vacuo to leave the acid chloride as a pale yellow solid, which was used without further purification.

To a stirred solution of methyl thioglycollate (4.5 ml, 0.05 mol) and triethylamine (8.3 ml, 0.055 mol) in dichloromethane (200 ml) at 0° C., under nitrogen, was added a solution of the crude acid chloride (11 g, 0.055 mol) in dichloromethane (200 ml) over 10 min. After addition was complete the mixture was allowed to warm to room temperature and stirred for 18 h. The mixture was evaporated in vacuo and ethyl acetate (100 ml) added to the residue. A white solid was filtered off and the filtrate washed with saturated sodium bicarbonate solution (2×50 ml), 1M hydrochloric acid (2×50 ml), water (50 ml) and brine (50 ml). The organic layer was separated, dried (MgSO$_4$) and evaporated in vacuo. The residue was chromatographed on silica gel, using 2:1 petrol:ethyl acetate as the eluant, to afford S-(3-nitrophenylacetyl)thiolacetic acid methyl ester (12.8 g, 95%) as a pale yellow oil. $^1$H NMR (360MHz, CDCl$_3$) δ3.73 (5H, 2 x s), 4.00 (2H, s), 7.53 (1H, dd, J =8 and 8Hz), 7.63 (1H, d, J=8Hz), 8.18 (3H, m). m/z (EI) 237 (M+).

Step 2: 4-Hydroxy-3-(3-nitrophenyl)-2(5H),thiophenone

To a stirred solution of S-(3-nitrophenylacetyl)thiolacetic acid methyl ester (10.8 g, 0.04 mol) in toluene (300 ml), at room temperature and under an atmosphere of nitrogen, was added 1,8-diazabicyclo[5.4.0]undec-7-ene (DBU) (6 ml, 0.04 mol) dropwise. The solution darkened and after 6 h the solution was partitioned between ethyl acetate (200 ml) and water (200 ml). The aqueous layer was separated and the organic phase washed once again with water (200 ml). The aqueous layers were combined, acidified to pill using 1M hydrochloric acid, and extracted with ethyl acetate (3×200 ml). The combined organic layers were dried (MgSO$_4$), evaporated in vacuo, and the residue triturated with ether (100 ml). 4-Hydroxy-3-(3-nitrophenyl)(2(5H)-thiophenone (1.32 g, 14%) was collected as a yellow solid. mp 248°–250° C. $^1$H NMR (360MHz, D$_6$-DMSO) δ4.11 (2H, s), 7.65 (1H, dd, J=8 and 8Hz), 8.06 (1H, dd, J =8 and 1.5Hz), 8.18 (1H, d, J =8Hz), 8.62 (1H, s).

Step 3: 3-( 3-Aminophenyl )-4-hydroxy-2( 5H)-thiophenone

A solution of 4-hydroxy-3-(3-nitrophenyl)-2(5H)-thiophenone (0.36 g, 1.5 mmol) in ethanol (70 ml) was hydrogenated at 40 psi using a palladium on carbon catalyst (200 mg, 55% ($^w/_w$)), for 10 min. The catalyst was filtered off and the solvent evaporated in vacuo. The brown residue was triturated with ether (10 ml) and methanol (0.5 ml). 3-(3-Aminophenyl)-4-hydroxy-2(5H)-thiophenone (208 mg, 67%) was isolated as a beige solid. mp 252°–254° C. (dec.). $^1$H NMR (360MHz, D$_6$-DMSO) δ3.88 (2H, s), 6.56 (1H, d, J=8Hz), 7.05 (1H, dd, J=8 and 8Hz), 7.13 (1H, d, J =8Hz), 7.21 (1H, s).

Step 4: (2-Acetamidophenyl) cyclohexyl methanone

Cyclohexylmagnesium bromide (240 ml of a 2M solution in ether, 0.48 mol) in ether (200 ml) was added dropwise to a solution of 2-methyl-4H-3,1-benzoxazin-4-one ( 100 g, 0.62 mol) in ether (1100 ml) at −10° C. over 2 h. The mixture was stirred at this temperature for 2 h, then at ambient temperature for 30 min. After cooling to −10° C. the suspension was treated with 2M HCl (600 ml), keeping the temperature below 0° C. After stirring for 15 rain the layers were separated, and the ethereal layer lo washed sequentially with water (500 ml), 5% sodium hydroxide solution (2×500 ml) and finally water (2×500 ml). The organic layer was separated, dried (MgSO$_4$), evaporated in vacuo and chromatographed on silica using petrol:ethyl acetate (2:1) to give (2-acetamidophenyl) cyclohexyl methanone (28 g, 24%) as a pale yellow solid. mp 66° C. ¹H NMR (CDCl₃, 360MHz) δ1.25–1.89 (10 H, m), 2.23 (3H, s), 3.33 (1H, m), 7.13 (1H, dt, J=6 and 1Hz), 7.53 (1H, dt, J=6 and 1Hz), 7.92 (1H, d, J=6Hz), 8.76 (1H, d, J=6Hz), 11.73 (1H, brs).

Step 5: (2-Aminophenyl) cyclohexyl methanone

A solution of (2-acetamidophenyl) cyclohexyl methanone (0.53 g, 2.16mmol) in methanol (5 ml) and concentrated hydrochloric acid (15 ml) was heated at 80° C. for 1 hour. After this time the solution was cooled to ambient temperature and the solvents removed in vacuo. The residue was dissolved in water (10 ml) and basified with 4N sodium hydroxide solution (20 ml). The mixture was then extracted into ethyl acetate (4×20 ml) and the organic layers combined and dried (MgSO₄). The solvent was evaporated and the residue chromatographed on silica in 2:1 petrol:ethyl acetate, to afford the amine (0.40 g, 91%) as a white solid. mp 73°–75° C. ¹H NMR (360MHz, CDCl₃) δ1.23–2.09 (10H, m), 3.27 (1H, m), 6.29 (2H, brs), 6.64 (2H, m), 7.25 (1H, dt, J=6 and 1Hz), 7.76 (1H, dd, J=7 and 1Hz).

An alternative procedure could be used for preparation of (2-aminophenyl) cyclohexyl methanone: To a cooled (0° C.) and stirred solution of 2-aminobenzonitrile (59.5 g, 0.5 mol) in anhydrous diethyl ether (210 ml) was added dropwise cyclohexylmagnesium chloride (2M in diethyl ether, 700 ml) at such a rate as to maintain the temperature below 25° C. After a further 18 h stirring at room temperature, the mixture was cooled to −60° C. and treated dropwise (CAUTION! highly exothermic reaction) with 5N hydrochloric acid (600 ml). The mixture was then allowed to warm to room temperature, diluted with additional 5N hydrochloric acid (500 ml) and the ethereal layer was separated. The acidic aqueous solution was basified to pH 4–5 with solid potassium hydroxide and then extracted with ethyl acetate (3×700 ml). The ethereal and ethyl acetate solutions were combined, washed with brine (1000 ml), dried (MgSO₄) and concentrated under vacuum to give the title compound (97 g, 94%) as a pale yellow solid.

Step 6:
5-Cyclohexyl-1,3-dihydro-3(R,S)-[(benzyloxycarbonyl)amino]-2H-1,4-benzodiazepin-2-one α-(Isopropylthio)-Nα-(benzyloxycarbonyl)-glycine (30 g, 0.11 mol) was dissolved in dichloromethane (1000 ml) and cooled to 0° C. The stirred solution was then treated with N-methyl morpholine (11.5 ml, 0.11 mol) followed by isobutyl chloroformate (13.7 ml, 0.11 mol). The resulting reaction mixture was stirred for a further 15 min at 0° C., then heated to reflux. The refluxing reaction mixture was treated dropwise, over 20 min, with a solution of (2-aminophenyl) cyclohexyl methanone (20.5 g, 0.1 mol) in dichloromethane (140 ml). After addition was complete the reaction was heated at reflux for a further 4 h. The mixture was then washed in succession with 10% citric acid solution (2×500 ml), saturated sodium bicarbonate solution (2×500 ml) and brine (500 ml). The dried (MgSO₄) organic phase was evaporated to afford the crude product as a pale orange solid, which was used without further purification.

The crude (isopropylthio)glycinamide was dissolved in anhydrous tetrahydrofuran (800 ml) and cooled to 0° C. Ammonia gas was bubbled through the stirred solution for 30 min before adding mercuric chloride (33 g, 0.12 mol) in one portion. Ammonia was continually bubbled through the solution for a further 5 hours, then the suspended solids were filtered off. The solvent was evaporated in vacuo to leave an oil, which was used without further purification.

The crude α-aminoglycinamide was dissolved in glacial acetic acid (500 ml) and treated with ammonium acetate (36.2 g, 0.47 mol). The resulting reaction mixture was stirred at room temperature overnight, before removing the solvent in vacuo. The residue was partitioned between ethyl acetate (300 ml) and 1N sodium hydroxide solution (300 ml). The organic phase was separated, dried (MgSO₄) and evaporated. The residue was chromatographed on silica, using 2:1 petrol:ethyl acetate as the eluant, to afford 5-cyclohexyl-1,3-dihydro-3(R,S)-[(benzyloxycarbonyl)-amino]-2H-1,4-benzodiazepin-2-one (25 g, 64%) as a white solid. mp 164°–166° C. ¹H NMR (360MHz, CDCl₃) δ1.07–2.04 (10H, m), 2.77 (1H, m), 5.12 (3H, m), 6.44 (1H, d, J=8Hz), 7.08 (1H, d, J=8Hz), 7.23–7.36 (6H, m), 7.46 (1H, t, J=7Hz), 7.59 (1H, d, J=8Hz), 8.60 (1H, brs).

Step 7: 5-Cyclohexyl-1,3-dihydro-1-methyl-3(R,S) [(benzyloxycarbonyl)amino]-2H-1,4-benzodiazepin-2-one A solution of 5-cyclohexyl-1,3-dihydro-3(R,S)-[(benzyloxycarbonyl)amino]-2H-1,4-benzodiazepin-2-one (1.1 g, 2.8 mmol) in dimethyl formamide (13 ml), under an atmosphere of nitrogen, was treated with sodium hydride (117 mg of a 55–60% dispersion in mineral oil, 2.8 mmol) in one portion, at −10° C. After 30 min at −10° C., iodomethane (174 μl, 2.8 mmol) was added in one portion and the solution allowed to reach 0° C. over 1 h. The solvent was then removed in vacuo and the crude residue partitioned between water (100 ml) and dichloromethane (100 ml). The organic phase was separated and the aqueous phase extracted with dichloromethane (2×100 ml). The combined organic layers were washed with brine, dried (MgSO₄) and evaporated. The residue was chromatographed on silica, using 1:1 petrol:ethyl acetate as the eluant, to afford the title compound (0.75 g, 66%) as a white solid. mp 205°–207° C. ¹H NMR (360MHz, CDCl₃) δ1.03–2.04 (10H, m), 2.76 (1H, m), 3.36 (3H, s), 5.10 (3H, m), 6.52 (1H, d, J=8Hz), 7.25–7.55 (9H, m).

Step 8:
3(R,S),Amino-5,Cyclohexyl-1,3-dihydro-1-methyl-2H-1,4-benzodiazepin-2-one 5-Cyclohexyl-1,3-dihydro-1-methyl-3(R,S)[(benzyloxycarbonyl)amino]-2H-1,4-benzodiazepin-2-one (1.5 g, 3.7 mmol) was dissolved in formic acid/methanol (200 ml of a 4 5% (ᵛ/ᵥ) solution), and added, over 5 min to a stirred suspension of 10% palladium on carbon (500 mg, 33% (ʷ/ʷ)) in formic acid/methanol (20 ml of a 4.5% (ᵛ/ᵥ) solution. After 1 h the catalyst was filtered off and washed sequentially with methanol and acetone. The filtrate was evaporated in vacuo and the residue partitioned between ethyl acetate (25 ml) and 10% sodium carbonate solution (25 ml). The organic phase was separated and the aqueous phase extracted with ethyl acetate (5×25 ml). The combined organic phases were dried (Na₂SO₄) and evaporated in vacuo to give a clear oil which was used without further purification.

An alternative procedure could be used for preparation of 3(R,S)- amino-5-cyclohexyl-1,3-dihydro-1-methyl-2H-1,4benzodiazepin-2-one:

A mixture of 5-cyclohexyl-1,3-dihydro-1-methyl-3(R,S)-[(benzyloxycarbonyl)amino]-2H-1,4-benzodiaze-2one (3.0 g, 7.4mmol) and hydrobromic acid (45% in acetic acid, 6.2 ml) was stirred for 1 h at room temperature under an atmosphere of nitrogen. The mixture was then diluted with cold anhydrous diethyl ether (40 ml) and stirred at 0° C. for 45 min. The white precipitate was collected by filtration, washed with cold diethyl ether (4×30 ml) and then dissolved in a mixture of water (30 ml) and aq. sodium hydroxide (2M, 15 ml). The basic aqueous phase was extracted with ethyl acetate (3×70 ml) and the combined organic layers were washed with brine (30 ml), dried ($Na_2SO_4$) and concentrated. The residue was chromatographed on silica gel, using 94:6, dichloromethane:methanol as the eluant, to afford the title compound (1.6 g, 80%) as a pale pink solid. mp 133°-136° C. $^1$H NMR (360MHz, $CDCl_3$) δ1.02–1.40 (4H, m), 1.47–1.56 (1H, m), 1.61–1.74 (3H, m), 1.84–1.91 (1H, m), 1.96–2.06 (1H, m), 2.17 (2H, brs), 2.70–2.80 (1H, m), 3.39 (3H, s), 4.29 (1H, s), 7.20–7.27 (2H, m), 7.44–7.54 (2H, m).

Step 9:
5-Cyclohexyl-1,3-dihydro-1-methyl-3(R,S)-[4nitronhenyloxycarbonyl)amino]-2H-1,4-benzodiazepin-2-one A solution of the amine (1 g, 3.7 mmol) in anhydrous tetrahydrofuran (20 ml) under an atmosphere of nitrogen at 0° C. was treated with triethylamine (0.51 ml, 3.7 mmol), followed by a solution of 4-nitrophenylchloroformate (0.75 g, 3.7 mmol) in anhydrous tetrahydrofuran (10 ml) dropwise. After stirring at ambient temperature for 20 min, the solid which precipitated from the mixture was filtered and the filtrate was evaporated in vacuo to leave a pink solid. The solid was triturated with diethyl ether to give the title compound (1.2 g, 75%) as a colourless solid. mp 165°-168° C. $^1$H NMR (360MHz, $CDCl_3$) δ1.05 (1H, m), 1.18–1.42 (3H, m), 1.55 (1H, m), 1.65 (3H, m), 1.87 (1H, m), 2.05 (1H, m), 2.80 (1H, m), 3.43 (3H, s), 5.18 (1H, d, J =8.3Hz), 6.90 (1H, d, J=8.2Hz), 7.30 (4H, m), 7.57 (2H,m), 8.23 (2H, d, J=7.1Hz).

Step 10:
N-[3(R,S)-5-Cyclohexyl-2,3-dihydro-1-methyl-2-oxo-1H-1,4-benzodiazenin-3-yl]N'-[3-(2,5-dihydro-4-hydroxy-2-oxothien-3-yl)phenyl]urea A solution of 5-cyclohexyl-1,3-dihydro-1-methyl-3(R,S)-[(4-nitrophenyloxycarbonyl)amino]-2H-1,4-benzodiazepin-2-one (Example 1, Step 9), (0.2 g, 0.46 mmol) in anhydrous dimethyl formamide (3 ml), under an atmosphere of nitrogen, at ambient temperature, was treated with triethylamine (63μl, 0.46retool). After stirring for 5 min, a solution of 3-(3-aminophenyl)-4-hydroxy-2(5H)-thiophenone (Example 1, Step 3) (100 mg, 0.48 mmol) in anhydrous dimethyl formamide (3 ml) was added dropwise. The yellow solution was then heated at 50° C. for 3 h. The solution was cooled to ambient temperature then partitioned between ethyl acetate (50 ml) and water (50 ml). The aqueous phase was separated and the organic phase extracted once more with water (50 ml). The combined aqueous layers were acidified to pill, using 1M hydrochloric acid, and extracted with ethyl acetate (3×50 ml). The combined organic layers were dried ($MgSO_4$) and evaporated in vacuo. The residue was azeotroped with toluene (2×20 ml) then the resultant solid triturated with methanol (10 ml). The solid was filtered and washed with diethyl ether. The title compound (150 mg, 65%) was obtained as a pink solid. mp 230° C. (dec.). $^1$H NMR (360MHz, $D_6$-DMSO) δ0.91 (1H, m), 1.14–1.88 (9H, m), 2.93 (1H, m), 3.32 (3H, s), 4.07 (2H, s), 5.06 (1H, d, J=8Hz), 7.10 (1H, d, J=8Hz), 7.18 (1H, dd, J=8 and 8Hz), 7.23 (1H, d, J=8Hz), 7.30–7.39 (2H, m), 7.48 (1H, s), 7.54 (1H, d, J=8Hz), 7.62 (1H, dd, J=8 and 7Hz), 7.74 (1H, d, J=8Hz), 8.99 (1H, s).

EXAMPLE 2

N-[3(R,S)-5-Cyclohexyl-2,3-dihydro-1-methyl-2-oxo-1H- 1,4-benzodiazepin-3-yl]N'-[3-( 2,5-dihydro-4-hydroxy-2-oxopyrrol-3-yl)phenyl]urea Step 1: (3-Nitrophenylacetyl)aminoacetic acid methyl ester To a stirred solution of 3-nitrophenylacetic acid (10 g, 0.055 mol), glycine methyl ester hydrochloride (7.3 g, 0,058 mol), triethylamine (8.0 ml, 0.058 mol) and 4-dimethylaminopyridine (7.1 g, 0,058 mol) in dichloromethane (200 ml) was added, under nitrogen, 1-( 3-dimethylaminopropyl )-3-ethylcarbodiimide(11.1 g, 0.058 mol), the mixture was stirred at room temperature for 18 h then the solvent removed in vacuo. Ethyl acetate (300 ml) was added to the residue and the mixture partitioned with 1M hydrochloric acid (2×200 ml), saturated sodium bicarbonate solution (2×200 ml), water (100 ml) and brine (100 ml). The organic phase was separated then evaporated in vacuo. The residue was triturated with ether (200 ml) to afford the desired amide (12.5 g, 90%) as a white solid. mp 104°-105° C. $^1$H NMR (360MHz, $CDCl_3$) δ3.71 (2H, s), 3.76 (3H, s), 4.06 (2H, d, J 5Hz), 6.06 (1H, br s), 7.53 (1H, dd, J=8 and 8Hz), 7.67 (1H, d, J =8Hz), 8.16 (2H, m).

Step 2:
1,5-Dihydro-4-hydroxy-3-(3-nitrophenyl)-2H-pyrrol-2-one

A suspension of (3-nitrophenylacetyl)aminoacetic acid methyl ester (13 g, 0.05 mol) in methanol (40 ml) and toluene (56 ml) was added to a stirred solution of sodium methoxide in methanol (prepared by dissolving sodium (1.5 g, 0,065 mol) in methanol (30 ml)), under nitrogen. The mixture was heated at reflux for 18 h. After this time more sodium methoxide in methanol (prepared by dissolving sodium (0.56 g, 0.024 mol)in methanol (15 ml)) was added and the mixture heated for a further 18 h. The solution was then cooled to ambient temperature and acetic acid added to pH5. The mixture was evaporated in vacuo and azeotroped with toluene (2×20 ml). The residue was chromatographed on silica gel, using 94:6:0.6 dichloromethane:methanol:acetic acid as the eluant, to afford the tetramic acid (2.8 g, 25%) as a yellow solid. mp 245°-247° C. (dec.). $^1$H NMR (360MHz, $D_6$-DMSO) δ3.85 (2H, s), 7.31 (1H, brs), 7.57 (1H, dd, J: 8 and 8Hz), 7.93 (1H, dd, J=8 and 1.5Hz), 8.60 (1H, d, J=8Hz), 9.08 (1H, s).

Step 3: 3-( 3-Aminophenyl)-1,5-dihydro-4-hydroxy-2H-pyrrol-2-one

A suspension of 1,5-dihydro-4-hydroxy-3-(3-nitrophenyl )-2H-pyrrol-2-one (0.6 g, 2.7 mmol) in methanol (30 ml) was hydrogenated at 30 psi using a palladium on carbon catalyst (200 mg, 35% ($^w/_w$)), for 10 min. The catalyst was filtered off and the solvent evaporated in vacuo. The residue was azeotroped with toluene (2×20 ml) and then triturated with ether (20 ml). 3-(3-Aminophenyl)-1,5-dihydro-4-hydroxy-2H- pyrrol-2-one (0.43 g, 84%) was isolated as a pale yellow solid. mp 262°–265° C. (dec.). $^1$H NMR (360MHz, D$_6$-DMSO) δ3.80 (2H, s), 6.37 (1H, d, J=8Hz), 6.93 (1H, dd, J=8 and 8Hz), 7.12 (1H, d, J =7Hz), 7.22 (1H, s), 7.45 (1H, s).

Step 4:
N-[3(R,S)-5-Cyclohexyl-2,3-dihydro,1-methyl-2-oxo-1H-1,4,benzodiazepin-3-yl]N'-[3-(2,5-dihydro-4-hydroxy-2-oxopyrrol-3-yl)phenyl]urea A solution of 5-cyclohexyl- 1,3-dihydro-1-methyl-3(R,S)-[(4-nitrophenyloxycarbonyl)amino]-2H-1,4-benzodiazepin-2-one (Example 1, Step 9) (0.3 g, 0.7 mmol) in anhydrous dimethyl formamide (4 ml), under an atmosphere of nitrogen, at ambient temperature, was treated with triethylamine (95 μl, 0.7 mmol). After stirring for 5min, a solution of 3-(3-aminophenyl)-1,5-dihydro-4-hydroxy-2H-pyrrol-2-one (Example 2, Step 3) (131 mg, 0.7 mmol) in anhydrous dimethylformamide (4 ml) was added dropwise. The yellow solution was then heated at 50° C. for 3 h. The solution was cooled to room temperature and the solvent evaporated in vacuo. The residue was partitioned between ethyl acetate (20 ml) and 20% aqueous acetic acid (20 ml). The organic layer was separated and the aqueous layer washed once more with ethyl acetate (20 ml). The combined organic layers were washed with brine (20 ml) then separated and dried MgSO$_4$). The solvent was removed in vacuo and the residue purified by chromatography on silica gel, using 94:6:0.6 dichloromethane:methanol:acetic acid as the eluant. The title compound (126 mg, 37%) was isolated as a white solid. mp 265°–270° C. (dec.). $^1$H NMR (360MHz, D$_6$-DMSO) δ0.90 (1H, m), 1.11–1.92 (9H, m), 2.92 (1H, m), 3.33 (3H, s), 3.76 (2H, s), 5.07 (1H, d, J=8Hz), 7.09 (2H, m), 7.23 (1H, d, J=8Hz), 7.36 (2H, m), 7.54 (1H, d, J=8Hz), 7.63 (2H, m), 7.75 (1H, d, J=7Hz), 7.88 (1H, s), 8.93 (1H, s).

EXAMPLE 3:
N-[3(R)-2,3-Dihydro-1-methyl-2-oxo-5-phenyl-1H-1,4-benzodiazepin-3-yl ]N'-[3-(2,5-dihydro-4-hydroxy-2-oxopyrrol-3-yl)phenyl]urea 3-(3-Aminophenyl)- 1,5-dihydro-4-hydroxy-2H-pyrrol-2-one (250 mg, 1.3 mmol) was suspended in anhydrous tetrahydrofuran (25 ml) and anhydrous dimethyl formamide (2 ml), under an atmosphere of nitrogen at 0° C. The stirred suspension was treated with triphosgene (128 mg, 0.43 mmol). The mixture was stirred at 0° C. for 2 min then triethylamine (0.54 ml, 3.93 mmol) was added, over a 5 min period. The mixture was stirred at 0° C. for a further 5 min then allowed to warm to ambient temperature and stirred for 10 min. The mixture was then cooled to 0° C. and a solution of 3(R)-amino-1,3-dihydro-1-methyl-5-phenyl-2H-1,4-benzodiazepin-2-one (238 mg, 0.9 mmol) in anhydrous tetrahydrofuran (4 ml) was added dropwise. The mixture was stirred at 0° C. for 5 min then allowed to warm to ambient temperature and stirred for 40 min. After this time the mixture was evaporated in vacuo and partitioned between water (30 ml) and ethyl acetate (30 ml). The aqueous phase was separated and washed once more with ethyl acetate (30 ml). The aqueous layer was separated, acidified to pill using 1M hydrochloric acid, then extracted with ethyl acetate (3×30 ml). The organic layers were combined, washed with brine (30 ml) then dried (Na$_2$SO$_4$). The solvent was removed in vacuo and the residue chromatographed on silica gel, using 94:6:0.6 dichloromethane:methanol:acetic acid followed by 90:10:1:1 dichloromethane:methanol:acetic acid:water as the eluant. The title compound (75 mg, 17%) was isolated as a white solid. mp 288°–292° C. (dec.). $^1$H NMR (360MHz, D$_6$-DMSO) δ3.40 (3H, s), 3.65 (2H, s), 525 (1H, d, J=8Hz), 6.74 (1H, brs), 7.06 (1H, dd, J=8 and 8Hz), 7.33–7.74 (12H, m), 7.97 (1H, s), 8.96 (1H, s).

EXAMPLE 4:
N-[3(R,S).5-Cyclohexyl-2,3-dihydro-1-methyl-2-oxo-1H-1,4-benzodiazepin-3-yl]N'-[3-(2,5-dihydro-4-hydroxy-N-methyl-2-oxolpyrrol-3-yl)phenyl]urea Intermediate 1:
3-(3-Aminophenyl)-1,5-dihydro-4-hydroxy-N-methyl-2H-pyrrol-2-one Step 1: N-Methyl-(3-nitrophenylacetyl)aminoacetic acid methyl ester To a stirred solution of 3-nitrophenylacetic acid (25 g, 0.14 mol), sarcosine methyl ester hydrochloride (20.2 g, 0.15 mol), triethylamine (20 ml, 0.15 mol) and 4-dimethylaminopyridine (17.7 g, 0.15 mol) in dichloromethane (300 ml) was added, under nitrogen, 1-(3-dimethylaminopropyl)-3-ethylcarbodiimide ( 27.8 g, 0.15 mol). The mixture was stirred at room temperature for 18 h then the solvent removed in vacuo. Ethyl acetate (300 ml) was added to the residue and the mixture partitioned with 1M HCl (2×200 ml), saturated sodium bicarbonate solution (2×200 ml), water (200 ml) and brine (200 ml). The organic phase was separated, dried (MgSO$_4$) and evaporated in vacuo. The residue was chromatographed on silica gel, using petrol:ethyl acetate (1:1) as the eluant, to afford the title amide (25 g, 68%) as a yellow oil. $^1$H NMR (360MHz, CDCl$_3$) δ3.13 (3H, s), 3.75 (3H, s), 3.88 (2H, s), 4.16 (2H, s), 7.26–7.65 (2H, m), 8.09–8.14 (2H, m). MS (CI, NH$_3$), 284 (M+NH$_4$+).

Step 2:
1,5-Dihydro-4-hydroxy-N-methyl-3-(3-nitrophenyl)-2H-pyrrol-2-one

A solution of the amide from Step I (3.0 g, 0.011 mol) in methanol (6 ml) was added, dropwise, to a stirred solution of sodium methoxide in methanol (prepared by dissolving sodium (1.21 g, 0.022 mol) in methanol (100 ml)) under nitrogen. The mixture was heated at reflux for 18 h then cooled to ambient temperature and the solvent removed in vacuo. The residue was partitioned between ethyl acetate (100 ml)and water (100 ml). The organic layer was separated and the aqueous layer washed once more with ethyl acetate (100 ml). The aqueous phase was then separated and acidified to pH2 using 1M aqueous hydrochloric acid. The resultant solid was filtered off, washed with water and then azeotroped with methanol (2×50 ml). The residue was triturated in anhydrous diethyl ether and the desired product (1.18 g, 46%) isolated as a yellow solid. $^1$H NMR (360MHz, D$_6$-DMSO) δ2.90 (3H, s), 4.01 (2H, s), 7.62 (1H, t, J=8Hz), 8.00 (1H, dd, J=8 and 2Hz), 8.51 (1H, d, J=8Hz), 9.00 (1H, t, J=2Hz). MS (CI, NH$_3$) 234 (M+).

Step 3: 3-( 3-Aminophenyl )-1,5-dihydro-4-hydroxy-N-methyl-2H-pyrrol-2-one

A suspension of 1,5-dihydro-4-hydroxy-N-methyl-3-(3-nitrophenyl)-2H-pyrrol-2-one (1.23 g, 5.3 mmol)in ethanol (70 ml) was hydrogenated at 40 psi using a palladium on carbon catalyst (300 mg, 24% (w/w)) for 30 min. The catalyst was filtered off and the solvent evaporated in vacuo. The residue was azeotroped with toluene (2×30 ml) and then triturated with anhydrous ether (30 ml). The tetramic acid (0.90 g, 83%) was isolated as a yellow solid. $^1$H NMR (360MHz, D$_6$-DMSO ) δ2.85 (3H, s), 3.87 (2H, s), 6.37 (1H, dd, J=7 and 1Hz), 6.93 (1H, t, J=8Hz), 7.12 (1H, d, J=8Hz), 7.20 (1H, t, J=2Hz). MS (CI, NH$_3$) 222 (M+NH$_4$+).

Step 4:
N-[3(R,S)-5-Cyclohexyl-2,3-dihydro-1-methyl-2-oxo-1H-1,4-benzodiazepin-3-yl]N'-[3-(2,5-dihydro-4-hydroxy-N-methyl-2-oxopyrrol-3-yl)phenyl]urea A solution of 5-cyclohexyl-l,3-dihydro-1-methyl-3(R,S)-[(4-nitrohenyloxycarbonyl)amino]-2H-1,4-benzodiazepin-2-one (Example 1, Step 9) (400 mg, 0.92 mmol) in anhydrous dimethylformamide (5.5 ml), under an atmosphere of nitrogen, at ambient temperature, was treated with triethylamine (126 μl 0.92 mmol). After stirring for 5 min, a solution of 3-(3-aminophenyl)-1,5-dihydro-4-hydroxy-N-methyl-2H-pyrrol-2-one (187 mg, 0.92 mmol) in anhydrous dimethylformamide (5.5 ml) was added dropwise. The solution was then heated at 50° C. for 2 h. The solution was cooled to room temperature and the solvent evaporated in vacuo. The residue was partitioned between ethyl acetate (20 ml) and 20% aqueous acetic acid (20 ml). The undissolved solid was filtered off and triturated with ether (20 ml) then hot methanol (20 ml), to afford the title compound (139 mg, 30%) as a white solid. mp 199°–201° C. $^1$H NMR (360MHz, D$_6$-DMSO) δ0.91 (1H, m), 1.09–1.93 (9H, m), 2.90 (4H, m), 3.31 (3H, s), 3.91 (2H, s), 5.07 (1H, d, J=8Hz), 7.13 (1H, t, J=8Hz), 7.23 (1H, d, J=8Hz), 7.36 (2H, m), 7.54 (2H, m), 7.63 (1H, m), 7.75 (1H, d, J=8Hz), 7.84 (1H, s), 8.96 (1H, s).

EXAMPLE 5:
N-[3(R)-5-Cyclohexyl-2,3-dihydro-1-methyl-2-oxo-1H-1,4-benzodiazepin-3-yl]N'-[3-(2,5-dihydro-4-hydroxy-N-methyl-2-oxopyrrol-3-yl)phenyl]urea Step 1:
3(R,S)-[2(R)-(tert-Butyloxycarbonvl)amino-3-phenyl-propionylamino]-5-cyclohexyl-1,3-dihydro-1-methyl-2H-1,4-benzodiazepin-2-one To a solution of 3(R,S)-amino-5-cyclohexyl-1,3-dihydro-1-methyl-2H-1,4-benzodiazepin-2-one (4 g, 14.8 mmol) in anhydrous dimethylformamide (35 ml), under an atmosphere of nitrogen, was added in succession Boc-D-phenylalanine (4.11 g, 15.4 mmol), 1-hydroxybenzotriazole trihydrate (2.09 g, 15.4 mmol) and 1-ethyl-3-[3-dimethylaminopropyl]carbodiimide hydrochloride (2.97 g, 15.4 mmol). Triethylamine (2.16 ml, 15.4 mmol) was then added and the resulting suspension was stirred at ambient temperature for 20 min. The solvent was removed under reduced pressure and the residue was partitioned between ethyl acetate (50 ml) and 10% citric acid solution (50 ml). The organic phase was separated and the aqueous phase extracted with ethyl acetate (3×50 ml). The combined organic phases were washed with 10% sodium hydroxide solution (50 ml), water (50 ml) and brine (50 ml), dried (MgSO$_4$) and evaporated in vacuo. The residue was chromatographed on silica gel, using 1:1 petrol:ethyl acetate as the eluant, to afford the product (7.26 g, 95%) as a pale yellow solid. mp 95°–98° C. $^1$H NMR (360MHz, CDCl$_3$) δ0.99–1.11 (1H, m), 1.16–1.72 (7H, m), 1.40 (9H, s), 1.83–1.92 (1H, m), 1.98–2.06 (1H, m), 2.73–2.83 (1H, m), 3.10–3.24 (2H, m), 3.38 (3H, s), 4.53 (1H, brs), 4.98 (1H, brs), 5.28–5.34 (2H, m), 7.19–7.32 (7H, m), 7.49–7.58 (2H, m).

Step 2:
(+)-3(R)-(2(R)-Amino-3-phenylnropionylamino)-5-cyclohexyl-1,3-dihydro-1-methyl -2H-1,4-benzodiazepin-2-one 3(R,S)-[2(R)-(tert-Butyloxycarbonyl)amino-3-phenylpropionylamino]-5-cyclohexyl-1,3-dihydro-1-methyl- 2H-1,4-benzodiazepin-2-one (4.7 g, 9.1 mmol) was dissolved in ethyl acetate (20 ml) and cooled to 0° C. This solution was then saturated with hydrogen chloride gas. After 1.5 h, the resulting precipitate (which was shown to be the undesired diastereoisomer, R$_f$=0.04 ethyl acetate), was removed by filtration and the filtrate evaporated. The solid residue was partitioned between ethyl acetate (25 ml) and 10% sodium carbonate solution (20 ml). The organic phase was separated and the aqueous extracted with ethyl acetate (2×25 ml). The combined organic phases were dried (Na$_2$SO$_4$) and evaporated in vacuo. The residue was chromatographed on silica gel using a gradient elution of 0–20% methanol in ethyl acetate to afford the title compound (1.66 g, 44%, R$_f$=0.13 ethyl acetate) as a pale yellow solid. mp 100°–103° C. $^1$H NMR (360MHz, CDCl$_3$) δ1.00–1.39 (4H, m), 1.50–1.72 (4H, m), 1.84–1.92 (1H, m), 2.00–2.07 (1H, m), 2.72–2.84 (2H, m), 3.28 (1H, dd, J=13.8 and 4.0Hz), 3.40 (3H, s), 3.69 (1H, dd, J=9.8 and 4.1Hz), 5.36 (1H, d, J=8.3Hz), 7.21–7.36 (7H, m), 7.47–7.58 (2H, m), 8.66 (1H, d, J=8.3Hz). [α]$_D^{23}$+32.7° (c=0.58, CH$_3$OH).

The undesired diastereoisomer (Rf 0.04, ethyl acetate) could be epimerised to 3(R,S)-(2(R)-amino-3-phenylpropionylamino)-5-cyclohexyl-1,3-dihydro-1-methyl-2H -1,4-benzodiazepin-2-one using the following procedure:

The undesired diastereoisomer (Rf 0.04, ethyl acetate) (18.6 g, 0.044 mol) was dissolved in anhydrous ether (200 ml), and potassium-tert-butoxide (0.68 g, 6.1 mmol) was added. The mixture was stirred at room temperature for 1 h, then more potassium-tert-butoxide (0.68 g, 6.1 mmol) was added and the mixture heated at reflux for 5 h. The mixture was then cooled to ambient temperature, the solvent removed under vacuum, and the residue partitioned between ethyl acetate (200 ml) and water (200 ml). The organic layer was separated, dried (MgSO$_4$), filtered and evaporated in vacuo to afford the epimerised material.

Step 3:
(+)-N-[1(R)-2-[(3(R)-5-Cyclohexyl-2,3-dihydro-1-methyl-2-oxo-1H-1,4-benzodiazepin-3-yl)amino]-2-oxo-1(phenylmethyl)ethyl]N'-phenyl thiourea A solution of (+)-3(R)-(2(R)-amino-3-phenylpropionylamino)-5-cyclohexyl-1,3-dihydro-1-methyl-2 H-1,4-benzodiazepin-2-one (1.6 g, 3.83 mmol) in anhydrous dichloromethane (10 ml) was treated with phenyl isothiocyanate (0.5 ml, 4.21 mmol), and then heated on the steam bath for 30 min. The solvent was evaporated in vacuo and the residue was chromatographed on silica gel with 1:1, ethyl acetate:petrol as the eluant, to afford the product (2.1 g, 100%) as a pale yellow solid. mp 129°–132° C. $^1$H NMR (360MHz, CDCl$_3$) δ0.95–1.07 (1H, m), 1.15–1.37 m), 1.45–1.69 (4H, m), 1.81–1.88 (1H, m), 1.93–2.00 (1H, m), 2.70–2.80 (1H, m), 3.24–3.41

(2H, m), 3.38 (3H, s), 5.23 (1H, d, J=7.3Hz), 5.31–5.40 (1H, m), 6.67 (1H, 7.0Hz), 6.87–7.02 (2H, m), 7.20–7.35 (9H, m), 7.46–7.52 (2H, m), 7.65 (1H, s). [α]$^{25}$$_D$+27.3° (c=0.31, CH$_2$Cl$_2$).

Step 4: 3(R )-Amino-5-cyclohexyl-1,3-dihydro-1-methyl-2H-1,4-benzodiazepin-2-one (+)-N-[1(R)-2-[(3(R)-5-Cyclohexyl-2,3-dihydro-1-methyl-2-oxo-1H-1,4-benzodiazepin-3-yl )amino]-2-oxo-1(phenylmethyl)ethyl]N'-phenyl thiourea (1 g, 1.8 mmol) was dissolved in trifluoroacetic acid (10 ml) and heated to 55° C. for 15 min. The trifluoroacetic acid was removed under reduced pressure and the residue azeotroped with dichloromethane (2×10 ml) and toluene (2×10 ml). The residue was chromatographed on silica gel using 90:10:0.1:0.1, dichloromethane:methanol:acetic acid:water as the eluant to afford an orange gum. This was dissolved in ethyl acetate (40 ml), cooled to 0° C., and treated with 10% sodium carbonate solution (3 ml). After stirring for I min, the organic layer was separated and the aqueous re-extracted with ethyl acetate (2×20 ml). The combined organics were dried (Na$_2$SO$_4$) and evaporated in vacuo to afford an orange solid. This was assumed to be the amine and was used without further purification.

Step 5:
N-[3(R)-5-Cyclohexyl-2,3-dihydro-1-methyl-2-oxo-1H-1,4-benzodiazepin-3-yl]N'-[3-(2,5-dihydro-4-hydroxy-N-methyl-2-oxolpyrrol-3-yl)phenyl]urea 3-(3-Aminophenyl )-1,5-dihydro-4-hydroxy-N-methyl-2H-pyrrol-2-one (548 mg, 2.7 mmol) was suspended in anhydrous tetrahydrofuran (50 ml), under an atmosphere of nitrogen. Triethylamine (0.37 ml, 2.7 mmol) was then added dropwise over 2 min and the mixture stirred for a further 5 min. The mixture was then cooled to 0° C. and triphosgene (264 mg, 0.89 mmol) was added and the mixture stirred for 2 min. Triethylamine (0.73 ml, 5.3 mmol) was then added over a 5 min period and the mixture stirred at 0° C. for a further 5 min. The cooling bath was removed and the mixture stirred at ambient temperature for 10 min. The mixture was then cooled back to 0° C. and a solution of 3(R )-amino-5-cyclohexyl-1,3-dihydro-1-methyl-2H-1,4-benzodiazepin-2-one (500 mg, 1.84 mmol) in anhydrous tetrahydrofuran (6 ml) was added dropwise. The mixture was stirred at 0° C. for 5 min then allowed to warm to room temperature and stirred for 30 min. The mixture was then evaporated in vacuo and the residue chromatographed on silica gel, using 94:6:0.6 dichloromethane:methanol:acetic acid as the eluant. The title compound (180 mg, 20%) was isolated as a white solid. mp 223°–225° C. $^1$H NMR (360MHz, D$_6$-DMSO) δ0.90 (1H, m), 1.07–1.89 (9H, m), 2.86 (3H, s), 2.93 (1H, m), 3.31 (3H, s), 3.90 (2H, s), 5.07 (1H, d, J=8Hz), 7.13 (1H, t, J=8Hz), 7.23 (1H, d, J=8Hz), 7.33–7.39 (2H, m), 7.53–7.55 (2H, m), 7.64 (1H, m), 7.75 (1H, d, J=8Hz), 7.83 (1H, s), 8.96 (1H, s).

EXAMPLE 6:
N-[3(R)-5-Cyclohexyl-2,3-dihydro-1-methyl-2-oxo-1H-1,4-benzodiazepin-3-yl]N'-[3-( 2,5-dihydro-4-hydroxy-2oxopyrrol-3-yl)phenyl]urea 3-(3-Aminophenyl)-1,5-dihydro-4-hydroxy-2H-pyrrol-2-one (409 mg, 2.15 mmol) was suspended in anhydrous tetrahydrofuran (40 ml), under an atmosphere of nitrogen. Triethylamine (296 μl, 2.14 mmol) was then added dropwise over rain and the mixture stirred for a further 2 min. The mixture was then cooled to 0° C. and triphosgene (210 mg, 0.71 mmol) was added and the mixture stirred for 2 min. Triethylamine (595 μl, 4.3 mmol) was then added over a 5 min period and the mixture stirred at 0° C. for a further 5 min. The cooling bath was removed and the mixture stirred at ambient temperature for 10 min. The mixture was then cooled back to 0° C. and a solution of (R)-amino-5-cyclohexyl-1,3-dihydro-1-methyl-2H-1,4-benzodiazepin-2-one (400 mg, 1.47 mmol) in anhydrous tetrahydrofuran (5 ml) was added dropwise. The mixture was stirred at 0° C. for 5 rain then allowed to warm to room temperature and stirred for 30 min. The residue was then evaporated in vacuo and the residue chromatographed on silica gel, using 94:6:0.6 dichloromethane:methanol:acetic acid as the eluant. The title compound (140 mg, 20%) was isolated as a white solid. mp 220° C. (dec.). $^1$H NMR (360MHz, D$_6$-DMSO) δ0.90 (1H, m), 1.09–1.91 (9H, m), 2.93 (1H, m), 3.32 (3H, s), 3.82 (2H, s), 5.07 (1H, d, J=8Hz), 7.13 (1H, t, J=8Hz), 7.23 (1H, d, J =8Hz), 7.35–7.39 (2H, m), 7.53–7.65 (3H, m), 7.74 (1H, d, J=8Hz), 7.85 (1H, s), 8.97 (1H, s).

EXAMPLE 7:
N-[3(R,S)-5-Cyclobutyl-2,3-dihydro-1-methyl-2-oxo-1H-1,4-benzodiazepin-3-yl]N'-[3-(2,5-dihydro-4-hydroxy-2-oxopyrrol-3-yl)phenyl]urea Step 1: 2-Aminophenyl cyclobutyl methanone Over a period of 1 h a solution of cyclobutyl bromide (13 g, 0.1 mol) in diethyl ether (150 ml) was added dropwise to a slurry of magnesium turnings (2.5 g, 0.11 mol)and a crystal of iodine in diethyl ether (20 ml) at reflux. The mixture was stirred for a further hour whereupon the Grignard solution was cannulated into a pressure equalising dropping funnel, attached to a three-necked round-bottomed flask, which was under an atmosphere of nitrogen.

A solution of 2-aminobenzonitrile (3.78 g, 32 mmol) at 0° C. in diethyl ether (50 ml) was treated dropwise with the Grignard reagent prepared above, over a period of 15 min. Once the addition was complete, the mixture was warmed to room temperature and stirred for 16 h under nitrogen. The solution was cooled to 0° C., quenched with 5N hydrochloric acid (20 ml), and basified using solid sodium hydroxide (4 g). The aqueous solution was extracted with ethyl acetate (2×100 ml) and the combined organic layers were dried (Na$_2$SO$_4$) and evaporated. The residue was chromatographed on silica gel using 2:1 petrol:ethyl acetate as the eluant. This gave a yellow oil which was then azeotroped with toluene (2×80 ml) to give the title compound (4 g, 71%) as a pale yellow solid. mp 55° C. $^1$H NMR (250MHz, CDCl$_3$) δ1.72–2.48 (6H, m), 3.80–4.00 (1H, m), 6.23 (2H, brs), 6.50–6.61 (2H, m), 7.11–7.22 (1H, m), 7.45–7.54 (1H, m).

Step 2:
5-Cyclobutyl-1,3-dihydro-3(R,S)-[(benzyloxycarbonyl )amino]-2H-1,4-benzodiazepin-2-one A solution of α-isopropylthio-N-benzyloxycarbonyl glycine (8.4 g, 29.7 mmol) in anhydrous dichloromethane (200 ml) was cooled to 0° C. N-Methylmorpholine (3.3 ml, 29.7 mmol) was added over 2 min followed by isobutyl chloroformate (3.9 ml, 29.7 mmol). This mixture was stirred for 15 min at 0° C. whereupon the mixture was heated to reflux. 2-Aminophenyl cyclobutyl methanone (4 g, 22.9 mmol) in anhydrous dichloromethane (20 ml) was added dropwise at reflux to the reaction mixture over 10 rain and the mixture stirred at reflux for a further 1.5 h. The reaction mixture was washed with 1N citric acid (100 ml), water (100 ml), saturated sodium bicarbonate solution (100 ml) and brine (100 ml). The organic phase was dried ($Na_2SO_4$), evaporated and azeotroped with toluene (2×100 ml) to give a yellow oil. Trituration with 7:1 petrol:ethyl acetate afforded the product (8 g, 80%) as a colourless solid. This material was used without further purification. A solution of anhydrous tetrahydrofuran (300 ml) was cooled to 0° C. and saturated with ammonia gas. To this solution was added the glycinamide (8 g, 18 mmol) prepared above, followed by mercuric chloride (7.4 g, 27 mmol). The mixture was stirred at 0° C. for 1.5 h with continuous bubbling of ammonia gas. The mixture was filtered through "hyflo" and the filtrate evaporated to afford the desired amine as a colourless waxy solid. The material was used without further purification.

The amine (6.9 g, 18 mmol) prepared above was dissolved in acetic acid (250 ml) and treated with ammonium acetate (6.5 g, 84.6 mmol). This mixture was stirred at room temperature for 16 h under nitrogen. The solvent was evaporated and the residue partitioned between ethyl acetate (250 ml) and 10% sodium hydroxide solution (100 ml). The organic layer was separated, dried ($Na_2SO_4$) and evaporated to give a yellow solid. Trituration with diethyl ether afforded the title compound (3.8 g, 50%) as a colourless solid. mp 200°–202° C. TLC (silica, petrol:ethyl acetate 2:1). Rf=0.3. $^1$H NMR (250MHz, $CDCl_3$) δ1.60–2.80 (6H, m), 3.70 (1H, m), 5.12 (2H, m), 5.22 (1H, d, J=8Hz), 6.50 (1H, d, J=8Hz), 7.02–7.53 (9H, m), 9.44 (1H, s).

Step 3:
5-Cyclobutyl-1,3-dihydro-1-propyl-3(R,S)-[(benzyl oxycarbonyl)amino]-2H-1,4-benzodiazepin -2-one A solution of 5-cyclobutyl-1,3-dihydro-3(R,S)-(benzyloxycarbonyl)amino]-2H-1,4-benzodiazepin-2-one (2.0 g, 5.51 mmol) in dimethylformamide (15 ml), under an atmosphere of nitrogen, was treated with sodium hydride (231 mg of a 55–60% dispersion in mineral oil, 5.79 mmol) in one portion, at −10° C. After 30 min at −10° C. 1-iodopropane (564 μl, 5.79 mmol) was added in one portion and the solution allowed to reach 0° C. over 1 h. The solvent was then removed in vacuo and the crude residue partitioned between water (100 ml) and dichloromethane (100 ml). The organic phase was separated and the aqueous phase extracted with dichloromethane (2×100 ml). The combined organic layers were washed with brine, dried ($MgSO_4$) and evaporated. The residue was chromatographed on silica gel, using 2:1 petrol:ethyl acetate as the eluant, to afford the title compound (1.4 g, 63%) as a colourless solid. Rf=0.30. NMR (250MHz, $CDCl_3$) δ0.90 (3H, t, J=8Hz), 1.20–2.15 (6H, m), 2.20–2.40 (1H, m), 2.41–2.60 (1H, m), 3.40–3.80 (2H, m), 4.20 4.40 (1H, m), 5.00–5.20 (3H, m), 6.60 (1H, d, J=9Hz), 7.20–7.52 (8H, m).

Step 4:
3(R,S)-Amino-5-cyclobutyl-1,3-dihydro-1-propyl-2H-1,4-benzodiazepin-2-one 5-Cyclobutyl-1,3-dihydro-3(R,S)-[(benzyloxycarbonyl)amino]-1-propyl-2H-1,4-benzodiazepin-2-one (1.5 g, 3.7 mmol) was treated with a solution of 30% hydrogen bromide in acetic acid (5 ml), and stirred for 20 min at room temperature. The mixture was then added dropwise onto cold (0° C.) diethyl ether (50 ml). A white solid was precipitated and filtered off. The solid was treated with 10% sodium hydroxide solution (50 ml), then extracted with ethyl acetate (80 ml). The organic layer was separated, dried ($Na_2SO_4$) and evaporated to give a colourless oil. This material was then used without further purification.

Step 5:
N-[3(R,S)-5-Cyclobutyl-2,3-dihydro-1-oxo-1-propyl-1H-1,4-benzodiazepin-3-yl ]N′-[3-(2,5-dihydro-4-hydroxy-2-oxonyrrol-3,yl)-phenyl]urea A suspension of 3-(3-aminophenyl)-1,5-dihydro-4-hydroxy-2H-pyrrol-2-one (593 mg, 2.90 mmol) in anhydrous tetrahydrofuran (45 ml) was treated with triethylamine (277 μl 1.99 mmol) and stirred at room temperature for 5 min. The solution was cooled to 0° C., treated with triphosgene (284 mg, 0.96 mmol) and stirred for a further 2 min. Triethylamine was added portionwise (7×1.22 mmol, 7×169 μl) and the mixture was warmed to room temperature over 15 min. The solution was re-cooled to 0° C. whereupon 3(R,S)-amino-5-cyclobutyl-1,3-dihydro-1-propyl-2H-1,4-benzodiazepin-2-one (540 mg, 1.99 mmol) in anhydrous tetrahydrofuran (5 ml) was added dropwise over 5 min. After stirring at 0° C. for a further 5 min the reaction was allowed to warm to room temperature over 1 h. The insoluble material was filtered off and the solvent evaporated. The residue was partitioned between aqueous acetic acid (20%, 20 ml) and ethyl acetate (20 ml). The organic phase was separated, dried ($Na_2SO_4$) and evaporated. The residue was chromatographed on silica gel using 90:10 dichloromethane:methanol as eluant to give the urea as an off-white solid. Trituration with hot methanol afforded the title compound (70 mg, 7%) as a colourless solid. mp 230° C. (dec.). $^1$H NMR (360MHz, $D_6$-DMSO) δ0.70 (3H, t, J=8Hz), 1.00–2.45 (9H, m), 2.85 (3H, s), 3.60–3.80 (1H, m), 3.90 (2H, s), 4.15–4.40 (1H, m), 5.05 (1H, d, J: 9Hz), 7.00–7.90 (9H, m), 9.00 (1H, s).

EXAMPLE 8A

Tablets containing 1–25 mg of compound

|  | Amount mg | | |
| --- | --- | --- | --- |
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

EXAMPLE 8B

Tablets containing 26–100 mg of compound

|  | Amount mg | | |
| --- | --- | --- | --- |
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

EXAMPLE 9

Parenteral injection

|  | Amount mg |
| --- | --- |
| Compound of formula (I) | 1 to 100 |
| Citric Acid Monohydrate | 0.75 |
| Sodium Phosphate | 4.5 |
| Sodium Chloride | 9 |
| Water for Injections | to 1 ml |

The sodium phosphate, citric acid monohydrate and sodium chloride are dissolved in a portion of the water. The compound of formula (I) is dissolved or suspended in the solution and made up to volume.

EXAMPLE 10

Topical formulation

|  | Amount mg |
| --- | --- |
| Compound of formula (I) | 1–10 |
| Emulsifying Wax | 30 |
| Liquid paraffin | 20 |
| White Soft Paraffin | to 100 |

The white soft paraffin is heated until molten. The liquid paraffin and emulsifying wax are incorporated and stirred until dissolved. The compound of formula (I) is added and stirring continued until dispersed. The mixture is then cooled until solid.

BIOLOGICAL ACTIVITY

1. CCK Receptor Binding (Pancreas)

CCK-8 sulphated was radiolabelled with $^{125}$I-Bolton Hunter reagent (2000 Ci/mmole). Receptor binding was performed according to Chang and Lotti (Proc. Natl. Acad. Sci. 8.3., 4923–4926, 1986) with minor modifications.

Male Sprague-Dawley rats (150–200 g) were sacrificed by decapitation. The whole pancreas was dissected free of fat tissue and was homogenized in 25 volumes of ice-cold 10 mMN-2-hydroxyethyl-piperazine-N'-2-ethane sulphonic acid (HEPES) buffer with 0.1% soya bean trypsin inhibitor (pH 7.4 at 25° C.) with a Kinematica Polytron. The homogenates were centrifuged at 47,800 g for 10 min. Pellets were resuspended in 10 volumes of binding assay buffer (20mM (HEPES)), 1 mM ethylene glycol-bis-($\beta$-aminoethylether-N,N'-tetraacetic acid) (EGTA), 5mM $MgCl_2$, 150 mM NaCl, bacitracin 0.25 mg/ml, soya bean trypsin inhibitor 0.1 mg/ml, and bovine serum albumin 2 mg/ml pH 6.5 at 25° C.) using a Teflon (trademark) homogenizer, 15 strokes at 500 rpm. The homogenate was further diluted in binding assay buffer to give a final concentration of 0.5 mg original wet weight/1 ml buffer. For the binding assay, 50 $\mu$l of buffer (for total binding) or unlabelled CCK-8 sulphated to give a final concentration of 1 $\mu$M (for nonspecific binding) or the compounds of Formula I (for determination of inhibition of $^{125}$I-CCK-8 binding) and 50 $\mu$l of 500 pM $^{125}$I-CCK-8 (i.e. 50 pM final concentration) were added to 400 $\mu$l of the membrane suspensions in microfuge tubes. All assays were run in duplicate. The reaction mixtures were incubated at 25° C. for 2 hours and the reaction terminated by rapid filtration (Brandell 24 well cell harvester) over Whatman GF/C filters, washing 3×4 mls with ice-cold 100 Mm NaCl. The radioactivity on the filters was counted with a LKB gamma counter.

2. CCK Receptor Binding (Brain)

CCK-8 sulphated was radiolabelled and the binding was performed according to the description for the pancreas method with minor modifications.

Male Hartley guinea pigs (300–500 g) were sacrificed by decapitation and the cortex was removed and homogenized in 25 mL ice-cold 0.32M sucrose. The homogenates were centrifuged at 1000 g for 10 minutes and the resulting supernatant was recentrifuged at 20,000 g for 20 minutes. The $P_2$ pellet was resuspended in binding assay buffer (20mM HEPES, 5 mM $MgCl_2$, 0.25 mg/ml bacitracin, 1 mM EGTA pH 6.5 at 25° C.), using a Teflon (trademark) homogenizer (5 strokes at 500 rpm) to give a final concentration of 10 mg original wet weight/1.2 ml buffer. For the binding assay, 50 $\mu$l of buffer (for total binding) or unlabelled CCK-8 sulphated to give a final concentration of 1 $\mu$M (for non-specific binding) or the compounds of Formula I (for determination of inhibition of $^{125}$I-CCK-8 binding) and 50 $\mu$l of 500 pM $^{125}$I-CCK-8 (i.e. final concentration of 50 pM) were added to 400 $\mu$l of the membrane suspensions in microfuge tubes. All assays were run in duplicate. The reaction mixtures were incubated at 25° C. for 2 hours and then the reaction was terminated by rapid filtration (Brandell 24 well cell harvester) on Whatman GF/C filters with 3×5 ml washes of cold 100 mM NaCl. The radioactivity on the filters was counted with a LKB gamma counter.

In Vitro Results

Effects of the Compounds of Formula I on $^{125}$I-CCK-8 receptor binding

The preferred compounds of Formula I are those which produced dose-dependent inhibition of specific $^{125}$I-CCK-8 binding as defined as the difference between total and non-specific (i.e. in the presence of 1 $\mu$M CCK) binding.

Drug displacement studies were performed with at least 10 concentrations of compounds of Formula I and the $IC_{50}$ values were determined by regression analysis $IC_{50}$ refers to the concentration of the compound required to inhibit 50% of specific binding of $^{125}$I-CCK-8.

The data in Table I were obtained for compounds of Formula I.

TABLE I

| CCK RECEPTOR BINDING RESULTS $IC_{50}$ (nM) | | |
| --- | --- | --- |
| Compound of Ex # | $^{125}$I-CCK Pancreas | $^{125}$I-CCK Brain |
| 1 | 13 | 3.9 |
| 2 | 7.5 | 2.9 |
| 3 | >3000 | 16 |
| 4 | 56 | 6.3 |
| 5 | 280 | 2.5 |
| 6 | 110 | 0.67 |

We claim:

1. A compound of formula (I):

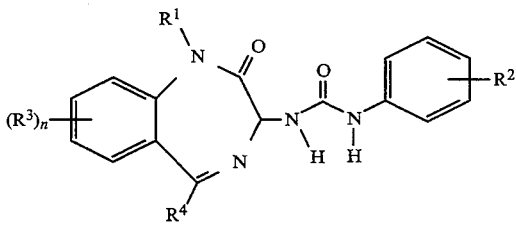

(I)

wherein:

$R^1$ is selected from H, $C_{1-6}$alkyl, $C_{3-7}$cycloalkyl, cyclopropylmethyl, $CH_2CO_2R^5$ (where $R^5$ is $C_{1-4}$alkyl) and $CH_2CONR^6R^7$ (where $R^6$ and $R^7$ are each independently selected from H and $C_{1-4}$alkyl, or $R^6$ and $R^7$ together form a chain $(CH_2)p$ where p is 4 or 5);

$R^2$ represents a group

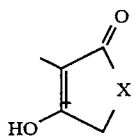

wherein:

X is selected from O, S and $NR^8$ where $R^8$ is selected from H and $C_{1-4}$alkyl;

each $R^3$ is selected from $C_{1-6}$alkyl, halo and $NR^6R^7$, where $R^6$ and $R^7$ are as previously defined;

$R^4$ is selected from $C_{1-7}$alkyl, $C_{3-7}$cycloalkyl, $C_{4-7}$cycloalkylalkyl, unsubstituted aryl and aryl substituted by one or more substituents selected from $C_{1-4}$alkyl, $C_{1-4}$alkoxy, hydroxy, halo and trifluoromethyl;

n is selected from 0, 1, 2 and 3;

or a salt or prodrug thereof.

2. A compound according to claim 1 wherein $R^1$ is selected from $C_{1-6}$alkyl, $C_{3-7}$cycloalkyl, cyclopropylmethyl, $CH_2CO_2R^5$ and $CH_2CONR^6RT$; $R^3$ is selected from $C_{1-6}$alkyl and halo; and n is selected from 0 and 1.

3. A compound according to claim 1 wherein X is $NR^8$.

4. A compound according to claim 1 wherein $R^4$ is $C_{3-7}$cycloalkyl.

5. A compound according to claim 1 selected from N-[3(R,S)-5-cyclohexyl-2,3-dihydro-1-methyl-2-oxo-1H-1,4-benzodiazepin-3-yl]N'-[3-(2,5-dihydro-4-hydroxy-2-oxothien-3-yl)phenyl]urea; N-[3(R,S)-5-cyclohexyl-2,3-dihydro-1-methyl-2-oxo-1H-1,4-benzodiazepin-3-yl]N'-[3-(2,5-dihydro-4-hydroxy-2-oxopyrrol-3-yl)phenyl]urea; N-[3(R,S)-2,3-dihydro-1-methyl-2-oxo-5-phenyl-1H-1,4-benzodiazepin-3-yl]N'-[3-(2,5-dihydro-4-hydroxy-2-oxopyrrol-3-yl)phenyl]urea; N-[3(R,S)-5-cyclohexyl-2,3-dihydro-1-methyl-2-oxo-1H-1,4-benzodiazepin-3-yl]N'-[3-(2,5-dihydro-4-hydroxy-N-methyl-2-oxopyrrol-3-yl)phenyl]urea; N-[3(R)-5-cyclohexyl-2,3-dihydro-1-methyl-2-oxo-1H-1,4-benzodiazepin-3-yl]N'-[3-(2,5-dihydro-4-hydroxy-N-methyl-2-oxopyrrol-3-yl)phenyl]urea; N-[3(R)-5-cyclohexyl-2,3-dihydro-1-methyl-2-oxo-1H-1,4-benzodiazepin-3-yl]N'-[3-(2,5-dihydro-4-hydroxy-2-oxopyrrol-3-yl)phenyl]urea; N-[3(R,S)-5-cyclobutyl-2,3-dihydro-1-methyl-2-oxo-1H-1,4-benzodiazepin-3-yl]N'-[3-(2,5-dihydro-4-hydroxy-2-oxopyrrol-3-yl)phenyl]urea; and salts and prodrugs thereof.

6. A pharmaceutical composition comprising a pharmaceutically effective amount of a compound according to claim 1 in association with a pharmaceutically acceptable carrier or excipient.

* * * * *